US00PP29200P2

(12) United States Plant Patent
Hansen et al.

(10) Patent No.: US PP29,200 P2
(45) Date of Patent: Apr. 3, 2018

(54) ***FESTUCA* PLANT NAMED 'BLUE WHISKERS'**

(50) Latin Name: ***Festuca glauca* (Vill.)**
Varietal Denomination: Blue Whiskers

(71) Applicants: Hans A. Hansen, Zeeland, MI (US); Kevin A. Hurd, Austin, TX (US)

(72) Inventors: Hans A. Hansen, Zeeland, MI (US); Kevin A. Hurd, Austin, TX (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/530,303

(22) Filed: Dec. 20, 2016

(51) Int. Cl.
*A01H 5/02* (2018.01)
*A01H 5/12* (2018.01)

(52) U.S. Cl.
USPC ..... Plt./384
CPC ..... *A01H 5/12* (2013.01)

(58) Field of Classification Search
USPC ..... Plt./384, 388
CPC ..... A01H 5/12
See application file for complete search history.

*Primary Examiner* — Kent L Bell

(57) ABSTRACT

The new and distinct cultivar of ornamental, winter-hardy, blue fescue plant, *Festuca glauca* 'Blue Whiskers', with highly-vigorous, clumps of tight, full, rounded habit of strong stems and foliage, consistent flower coverage, intensely silver-blue, linear, evergreen foliage retained throughout the year, upright habit of strong erect stems, long flowering season of large, densely-arranged, lavender-blue flowers on short branched stems.

1 Drawing Sheet

Botanical classification: *Festuca glauca* (Vill.).
Variety denomination: 'Blue Whiskers'.

BACKGROUND OF THE INVENTION

The present invention relates to a new and distinct plant of blue fescue, botanically known as *Festuca glauca* 'Blue Whiskers' and will be referred to hereinafter also by solely its cultivar name and the new plant.

*Festuca* 'Blue Whiskers' is a single seedling selected from seeds of open pollinated *Festuca glauca* 'Siskiyou Blue' with several other *Festuca* species, cultivars and selections in an isolated block collected by the inventors on Jun. 28, 2010 at a wholesale perennial nursery in Zeeland, Mich. All subsequent evaluations were performed in a full-sun trial garden at the same nursery with loamy sand soil and irrigation and fertilizer as required. The single seedling plant was selected for further evaluation during the summer of 2011 and assigned the breeder designation "HK10-02-05." The plant was propagated by division at the same nursery in Zeeland, Mich. and the original plant and the divisions evaluated over the next four years until final approval for introduction in the summer of 2015. The resultant asexually propagated divisions have been stable and identical to the original plant in successive asexual propagations.

No plants of *Festuca* 'Blue Whiskers' have been sold in this country, under this or any name, or anywhere in the world, prior to the filing of this application, nor has any disclosure of the new plant been made prior to the filing of this application with the exception of that which was disclosed within one year of the filing of this application and was derived either directly or indirectly from the inventor.

SUMMARY OF THE INVENTION

*Festuca glauca* 'Blue Whiskers' differs from its parent as well as all other hardy blue fescue known to the inventor in a combination of traits. The following characteristics in combination distinguish 'Blue Whiskers' from all other blue fescue plants known to the inventor:

1. Tight, full, rounded habit with strong foliage and stems;
2. Consistent flower coverage;
3. Intense silvery-blue, linear foliage retained throughout growing season.
4. Highly-vigorous clumps.

The nearest comparison plants known to the inventor are the seed parent plant *Festuca* 'Siskiyou Blue' (not patented) and 'Elijah Blue' (not patented). Compared to the seed parent, the new cultivar is shorter and wider. Compared to 'Elijah Blue' the new plant is taller, wider in habit and more vigorous. Compared to the cultivar 'Casca11' U.S. Plant Pat. No. 23,307 the new plant is shorter and narrower in habit with less drooping foliage.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
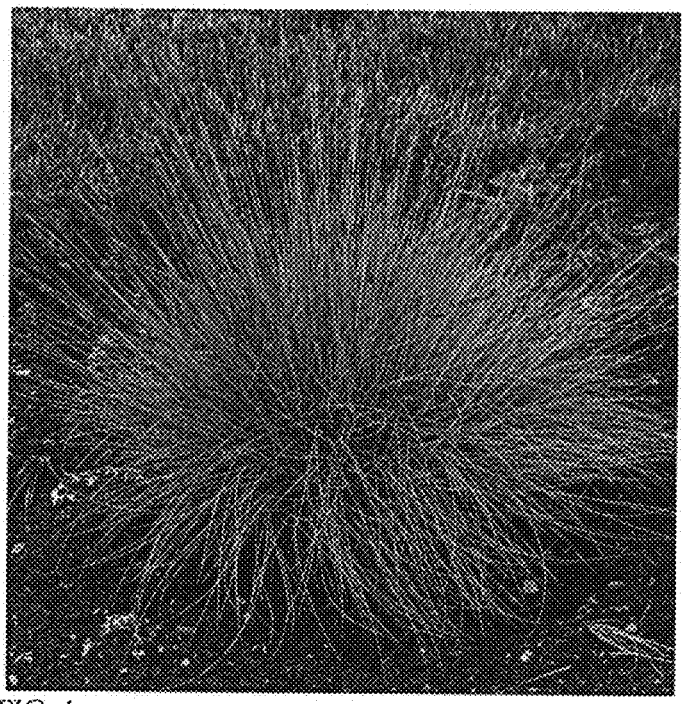
FIG. 1 shows a three-year-old plant of 'Blue Whiskers' in the landscape in early flower.
Figure 2:
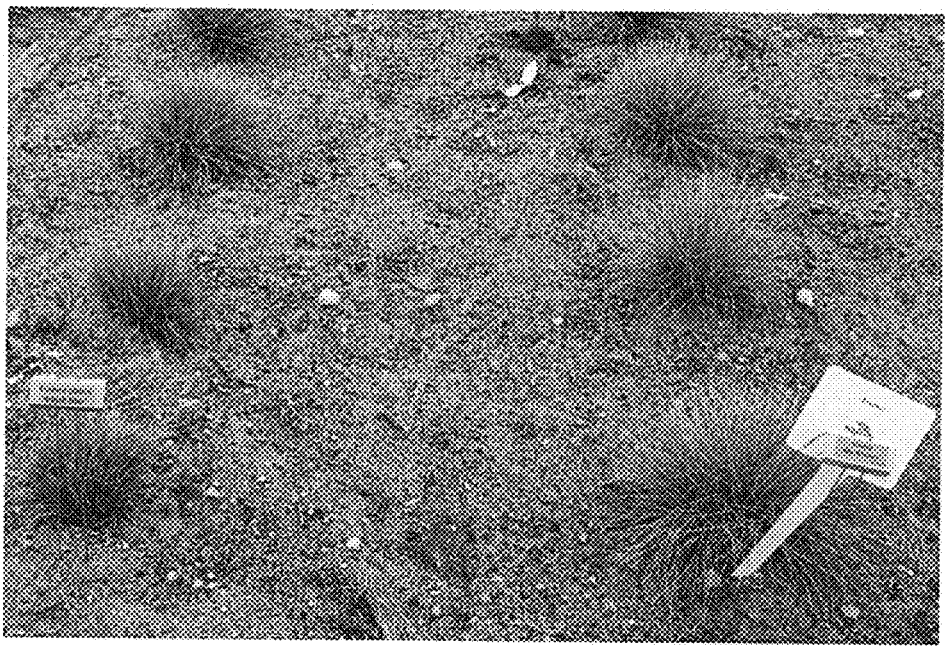
FIG. 2 shows a comparison of taller one-year-old plant of 'Blue Whiskers' (on the right) and the shorter one-year-old plants of 'Elijah Blue' (on the left).

The following is a detailed description of *Festuca glauca* 'Blue Whiskers' as observed and compared to other cultivars for three years in trial gardens and production fields at a nursery in Zeeland, Mich. The following description is of a three-year-old plant of 'Blue Whiskers' in a full-sun display garden in Zeeland, Mich. with limited supplemental fertilizer and irrigation as needed and without any pinching or plant growth regulators. The new plant has not been observed under all possible environments, and the phenotype may vary slightly with different environmental conditions, such as temperature, light, fertility, moisture and maturity levels, but without any change in the genotype. The color descriptions are in accordance with the 2001 edition of The R.H.S. Colour Chart of The Royal Horticultural Society, London, England, except where common dictionary color terms are used.

Plant habit: Winter-hardy herbaceous perennial with dense mounded habit;

Plant size: Foliage to about 23.0 cm tall and 42.0 cm across, about 33.0 cm in height with flower stems, width about 45 cm slightly above soil;

Root description: Fibrous; color nearest RHS 155D;

Propagation: Division; finishing in 3 liter container in about 3 months during summer production;

Growth rate: Vigorous;

Crop time: Finishing in 3-liter container from a division in about 3 months during summer production;

Shoots and branches: Plant shoots developing from base with no branches; about 160 flowering shoots per plant;

Leaves: Linear, slightly arching; conduplicate; apex narrowly acute; base decurrent, sheathed; margin entire; surfaces glaucous and glabrous; about four leaves per shoot; persistent and evergreen through winter in Zeeland, Mich.;

Leaf size: Average about 17 cm long and 1.0 mm across;

Leaf color: Young emerging leaves abaxial and adaxial nearest RHS 138A; older leaves abaxial and adaxial with glaucous covering removed between RHS 137A and RHS 138A; older leaves abaxial and adaxial without glaucous covering removed nearest RHS 122C;

Sheath: About 26.0 cm long and 2.0 mm across; color nearest RHS 138D with base nearest RHS 145D;

Venation: Parallel;

Internode length: Covered with sheath; average about 2.0 mm;

Culm: About 10.0 to 12.0 mm long; flattened longitudinally with folds of leaves;

Rachis: Lightly branched panicle in lower one-third; terete; stiff; attitude upright and outright;

Rachis color: Nearest RHS 122C;

Pedicel: Terete, thin, stiff; about 2.0 mm long and 0.5 mm diameter;

Pedicel color: Nearest RHS N138C;

Spikelet: About 10.0 mm long, about 2.5 mm wide and about 1.5 mm thick;

Rachilla: Terete; stiff; color nearest RHS N138C;

Awn: Numerous; stiff; color nearest RHS 164C;

Glume: Acute apex and truncate base; slightly glabrous and glaucous; about 2.5 mm long and about 1.0 mm across;

Glume color: Between RHS 163A and RHS 163B;

Fragrance: None detected;

Lemma: Slightly glabrous and glaucous; about 2.0 mm long and about 1.5 mm across;

Gynoecium: Protruding from lemma;

*Style*.—About 3.0 mm long and less than about 0.5 mm wide; color of base white, lighter than RHS 155D and distal about 1.0 mm nearest RHS N77C.

*Stigma*.—No yet observed.

Androecium: Protruding from lemma;

*Filaments*.—Exserted about 1.0 mm outside lemma, thin, flexible; about 0.2 mm in diameter; color nearest RHS 155D.

*Anther*.—About 1.5 mm long and 0.5 mm across, versatile; color nearest RHS 161B.

*Pollen*.—Abundant on fertile anthers; color nearest RHS 161B.

Seeds have not yet been observed;

Hardiness to at least U.S.D.A. zones 4 to 8; the new plant is very resistant to drought once established and even tolerant of clay soils if good drainage is provided;

Pest and disease resistance: No other susceptibility or resistance to diseases or pests has been observed except that which is common to blue fescue.

It is claimed:

1. A new and distinct cultivar of blue fescue plant, *Festuca glauca* 'Blue Whiskers' as herein described and illustrated.

* * * * *